United States Patent [19]

Sussman

[11] Patent Number: 5,281,227
[45] Date of Patent: Jan. 25, 1994

[54] LENS CASE WITH IOL FOLDING DEVICE

[75] Inventor: Glenn Sussman, Lake Forest, Calif.

[73] Assignee: Allergan, Inc., Irvine, Calif.

[21] Appl. No.: 973,438

[22] Filed: Nov. 9, 1992

[51] Int. Cl.⁵ .......................... A61B 17/00; A61F 9/00
[52] U.S. Cl. ..................... 606/107; 128/898; 206/5.1
[58] Field of Search ............. 206/5, 5.1, 6, 438; 606/1, 107; 623/4, 6; 128/897, 898

[56] References Cited

U.S. PATENT DOCUMENTS

| | | |
|---|---|---|
| 4,173,281 | 11/1979 | Trought ............... 206/5.1 |
| 4,257,521 | 3/1981 | Poler . |
| 4,269,307 | 5/1981 | LaHaye ............... 206/5.1 |
| 4,615,703 | 10/1986 | Callahan et al. ...... 606/107 |
| 4,697,697 | 10/1987 | Graham et al. . |
| 4,736,836 | 4/1988 | Alongi et al. . |
| 4,906,247 | 3/1990 | Fritch . |
| 4,911,158 | 3/1990 | Weatherly . |
| 5,007,913 | 4/1991 | Dulebohn et al. . |
| 5,100,410 | 3/1992 | Dulebohn . |
| 5,171,241 | 12/1992 | Buboltz et al. ....... 606/107 |
| 5,176,686 | 1/1993 | Poley ................ 606/107 |
| 5,190,553 | 3/1993 | Kanert et al. ........ 606/107 |

FOREIGN PATENT DOCUMENTS 4039119  9/1991  Fed. Rep. of Germany .

OTHER PUBLICATIONS

"Folding Techniques for the AMO SI-30 Intraocular Lens", 3 pages.

*Primary Examiner*—Stephen C. Pellegrino
*Assistant Examiner*—Glenn K. Dawson
*Attorney, Agent, or Firm*—Gordon L. Peterson

[57] ABSTRACT

A lens case for an intraocular lens having a deformable optic, including a folder for receiving the intraocular lens and folding the deformable optic about a fold axis. A retainer adjacent the folder holds the intraocular lens against substantial pivotal movement relative to the retainer about a pivot axis which is generally transverse to the fold axis. The folder and retainer are relatively pivotable about the pivot axis so that the orientation of the fold axis relative to the retainer and the deformable optic can be changed.

19 Claims, 4 Drawing Sheets

LENS CASE WITH IOL FOLDING DEVICE

FIELD OF THE INVENTION

This invention relates to a lens case for an intraocular lens (IOL) and more particularly to such a lens case having a feature which permits folding of a deformable optic about any one of a plurality of fold axes.

BACKGROUND OF THE INVENTION

IOL's are commonly used to replace the natural lens of the human eye when the natural lens becomes sufficiently ineffective in focusing light on the retina. To accomplish this, the natural lens is removed through an incision in the eye, and the intraocular lens is inserted into the eye through the incision. This is all accomplished using known surgical techniques.

An IOL typically includes an optic and one or more fixation members for fixing the optic in the eye along the optical axis of the eye. The optic may be either hard and nondeformable or soft and deformable. The deformable optic is foldable about a fold axis and can be inserted through the incision into the eye in the folded condition. This has the advantage of requiring a shorter incision as compared with the length of the incision required for the insertion of an IOL having a hard or nondeformable optic. Once inserted, the deformable optic has sufficient resilience to return to its unfolded or undeformed state.

IOL's have small dimensions, e.g. the optic may be about 6 mm in diameter, and therefore are not easy to accurately fold. Many folding devices are known for folding of deformable optics.

It has been found that different surgeons prefer to fold the deformable optic about different fold axes. For example, in the case of an IOL having diametrically opposed fixation members extending from the deformable optic at about the 1:30 o'clock and 7:30 o'clock positions, some surgeons prefer to fold the optic along a fold axis extending from about 3 o'clock to about 9 o'clock. Other surgeons prefer a fold having a fold axis extending from about 6 o'clock to about 12 o'clock. Still other surgeons may prefer a fold axis having another angular orientation relative to the fixation members.

The folding devices of which we are aware do not permit the surgeon to fold the optic about any one of a plurality of fold axes without removing the IOL from the folding device, reorienting the IOL and replacing the IOL into the folding device. Handling of the IOL increases the risk of damage to the IOL and loss of sterility. Although a forceps can accomplish folding of the IOL about a selected fold axis, the IOL must first be loaded into the forceps in the correct orientation, and this is difficult to accomplish primarily because of the small dimensions of the IOL and the resilience of the IOL.

SUMMARY OF THE INVENTION

This invention solves these problems. With this invention, the fold axis for a deformable optic can be easily selected by the surgeon while the IOL is being held by a lens case. Thus, fold axis selection does not require removal of the IOL from the lens case or handling of the IOL.

This invention provides a lens case which includes a folder for receiving an IOL and folding the deformable optic about a fold axis. Typically, the IOL is loaded into the lens case at the manufacturer's plant. A retainer is provided adjacent the folder for holding the IOL against substantial pivotal movement relative to the retainer about a pivot axis which is generally transverse to the fold axis. In order to permit the surgeon to change the orientation of the fold axis, the folder and retainer are relatively pivotable about the pivot axis. As a consequence, the orientation of the fold axis relative to the retainer and to the IOL can be changed.

The folder can be of various constructions. However, preferably the folder receives the IOL in a way to allow relative pivotal movement between the folder and the IOL about the pivot axis. This may be accomplished, for example, by providing a folder which includes jaws which loosely receive and support the IOL for pivotal movement about the pivot axis relative to the folder.

The folder also is capable of folding the deformable optic about the fold axis. Although this can be accomplished in different ways, preferably the jaws are relatively movable to fold the deformable optic about the fold axis.

The retainer may hold the IOL against substantial pivotal movement relative to the retainer about the pivot axis in various different ways. Preferably, this is accomplished by retaining the fixation members against such pivotal movement. In a preferred construction this is accomplished by the retainer having a fixation member receiving section for receiving a fixation member of the IOL and holding the fixation member to thereby hold the IOL against substantial pivotal movement relative to the retainer about the pivot axis. The jaws preferably receive and support the deformable optic at a location radially inwardly of the fixation member receiving section.

Various constructions and techniques can be employed to provide for the relative pivotal movement between the folder and the retainer about the pivot axis. Preferably the folder is mounted for pivotal movement on the retainer and this may be accomplished, for example, by cooperating surfaces on the retainer and folder. In one preferred construction, the retainer has a cavity and the folder has a bearing surface receivable in said cavity to mount the folder and retainer for relative pivotal movement about the pivot axis.

To facilitate handling, the lens case preferably includes a base and the folder is mounted on the base for pivotal movement relative to the base about the pivot axis. Preferably the base includes the retainer. The base may be used to aid the surgeon in selecting the desired fold axis. This can be accomplished, for example, by providing the base with a curved wall which at least partially circumscribes the retainer. The lens case includes a detent system on the curved wall and the folder for releasably retaining the folder in any of first and second predetermined angular positions about the pivot axis to thereby change the orientation of the fold axis relative to the support and to the IOL.

The lens case preferably includes a cap removably mounted on the base and having a cap portion overlying the retainer and at least a portion of the folder. The cap holds the IOL and folder on the base and protects the IOL.

The features of this invention may be embodied in a lens case or in an IOL package which includes the lens case and an IOL in the lens case.

This invention also has method features. The method may include supporting the IOL in a first angular position about a pivot axis relative to an IOL folder so that the IOL folder can fold a foldable or deformable optic about a first fold axis. The IOL is retained against substantial pivotal movement about the pivot axis relative to a retainer. The IOL folder is pivoted relative to the retainer and the IOL about the pivot axis to a second angular position so that the IOL folder can fold the foldable optic about a second fold axis. The foldable optic is then folded about the second fold axis using the IOL folder and the IOL is then removed in the folded condition from the IOL folder.

Preferably jaws of a forceps are placed into the IOL folder adjacent the foldable optic and the step of folding includes moving portions of the IOL folder toward each other to move the jaws of the forceps toward each other and to fold the foldable optic about the second fold axis. In this event, the step of removing includes removing the foldable optic in a folded condition from the IOL folder using the forceps. In this manner, the fold axis for the foldable optic is determined by the adjustment of the lens case, and the forceps simply removes the folded or partially folded IOL from the lens case. Another feature of this invention is that the folder can be separated from the retainer after the pivot axis has been oriented and before the foldable optic has been folded. This facilitates manipulation of the folder and folding of the optic.

The invention, together with additional features and advantages thereof may best be understood by reference to the following description taken in connection with the accompanying illustrative drawings.

DESCRIPTION OF THE PREFERRED EMBODIMENTS

Figure 1:
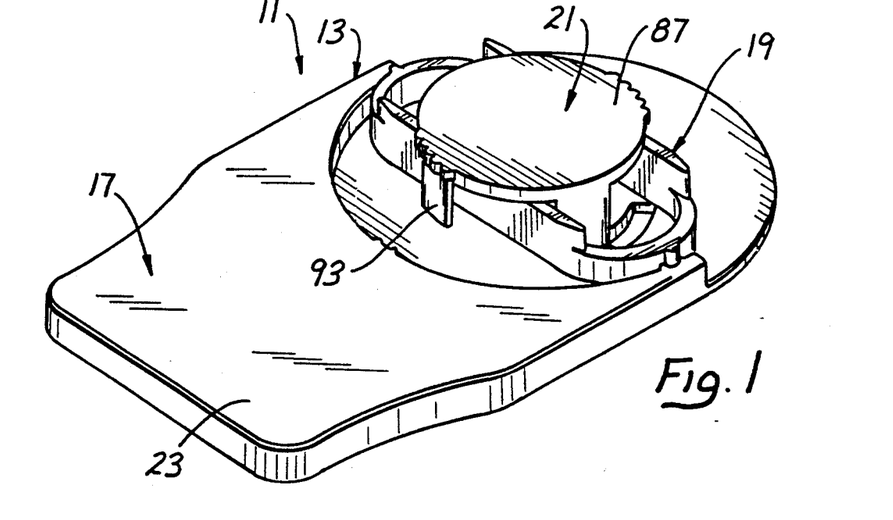
FIG. 1 is a perspective view of a lens case constructed in accordance with the teachings of this invention.
Figure 3:
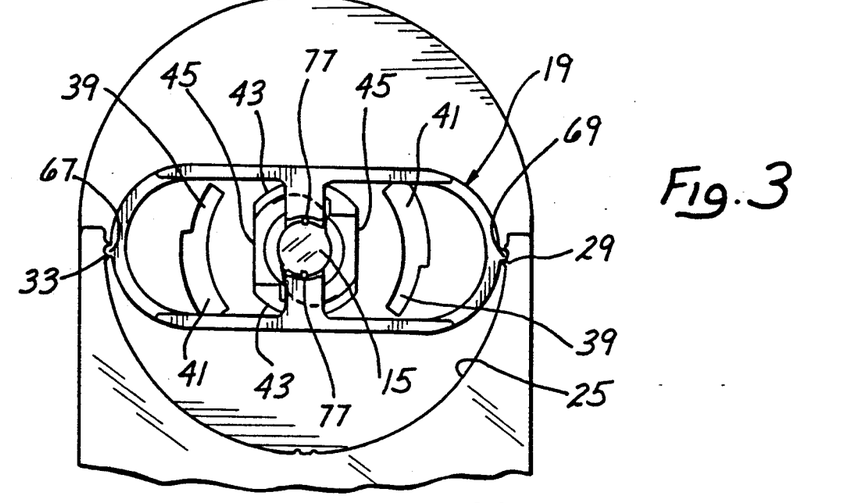
FIG. 3 is a fragmentary top plan view of the lens case and IOL with the cap removed.

FIG. 1 shows an IOL package 11 which generally comprises a lens case 13 and an IOL 15 (FIG. 3). The lens case 13 includes a rigid base 17, an IOL folder 19 and a cap 21. The base 17, the folder 19 and the cap 21 may each be integrally molded of a suitable polymeric material, such as polypropylene. If desired, the IOL package 11 can be sealed in a sterile container (not shown) and used for shipment and storage of the IOL 15.

The base 17 includes a tab or holding portion 23 at one end and a curved wall 25 partially surrounding a recessed portion 27 of the base 17. In this embodiment, the curved wall 25 extends for approximately 180 degrees and is provided with three sets of grooves 29, 31 and 33 spaced apart 90 degrees along the curved wall.

A retainer 35 projects upwardly (in the position shown in FIG. 2) from the recessed portion 27 in spaced relationship to the curved wall 25 and curved bayonet slots 37 are provided in the recessed portion 27 on opposite sides of the retainer 35. As shown more clearly in FIG. 3, each of the slots 37 has a narrow portion 39 and a wide portion 41 arranged such that the portions 39 are diametrically opposed and the portions 41 are diametrically opposed.

Figure 2:
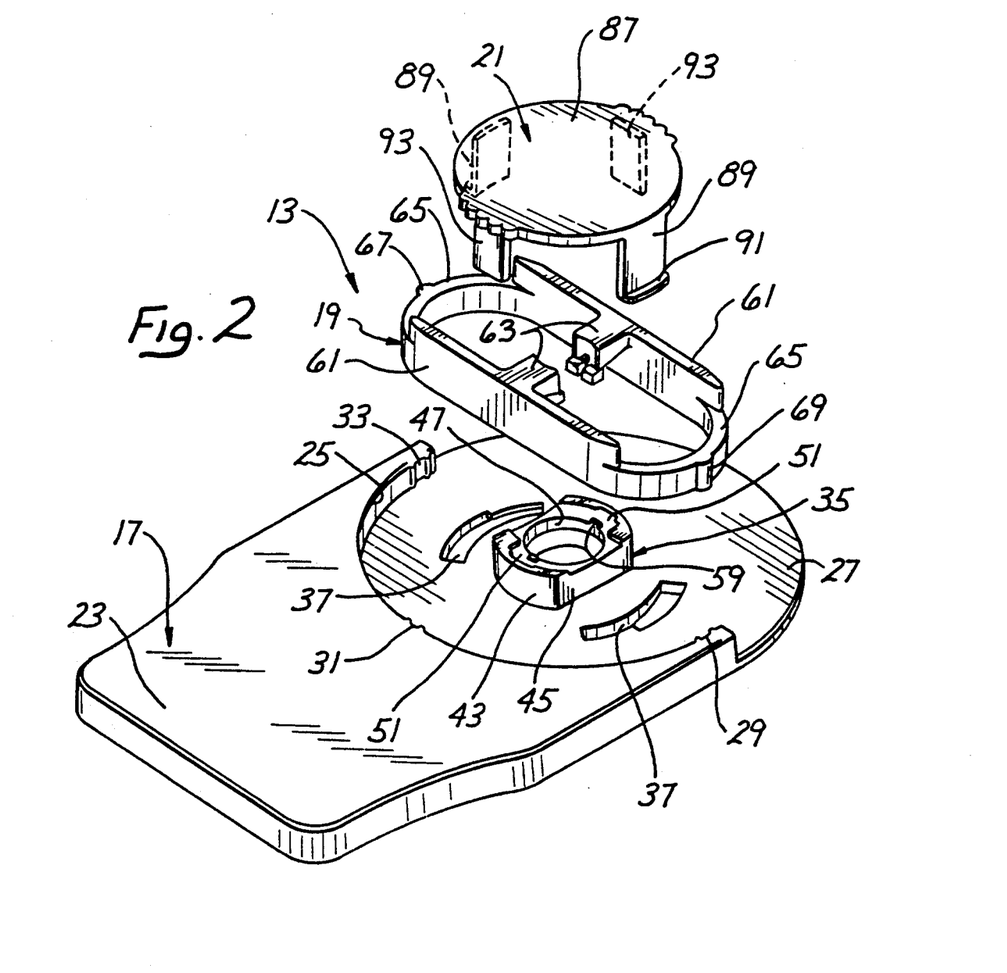
FIG. 2 is an exploded perspective view similar to FIG. 1.
Figure 4:
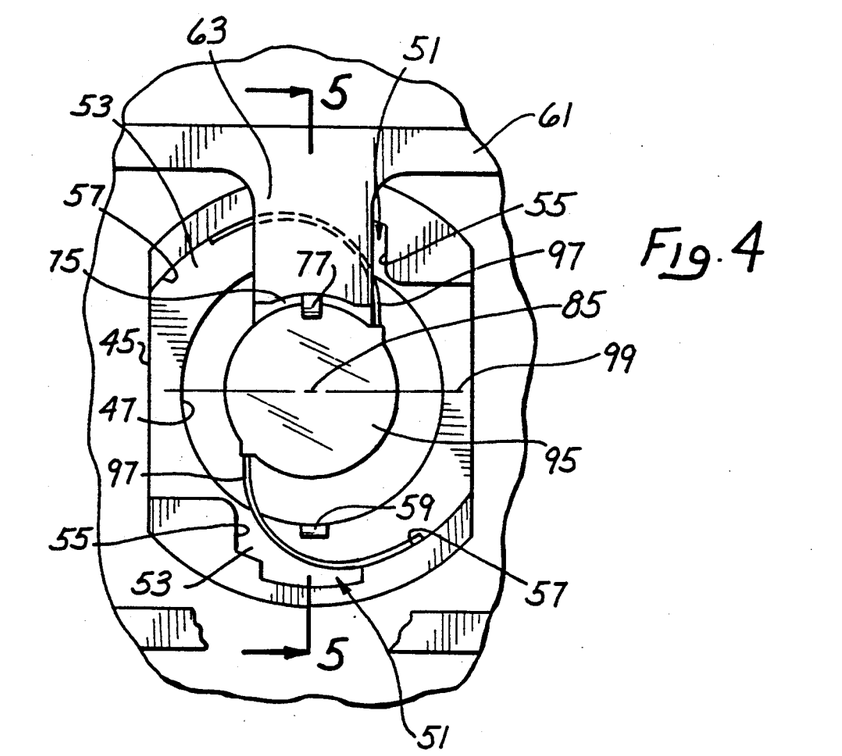
FIG. 4 is an enlarged fragmentary view of the portion of FIG. 3 adjacent the IOL with portions of the folder broken away.
Figures 5, 5A:
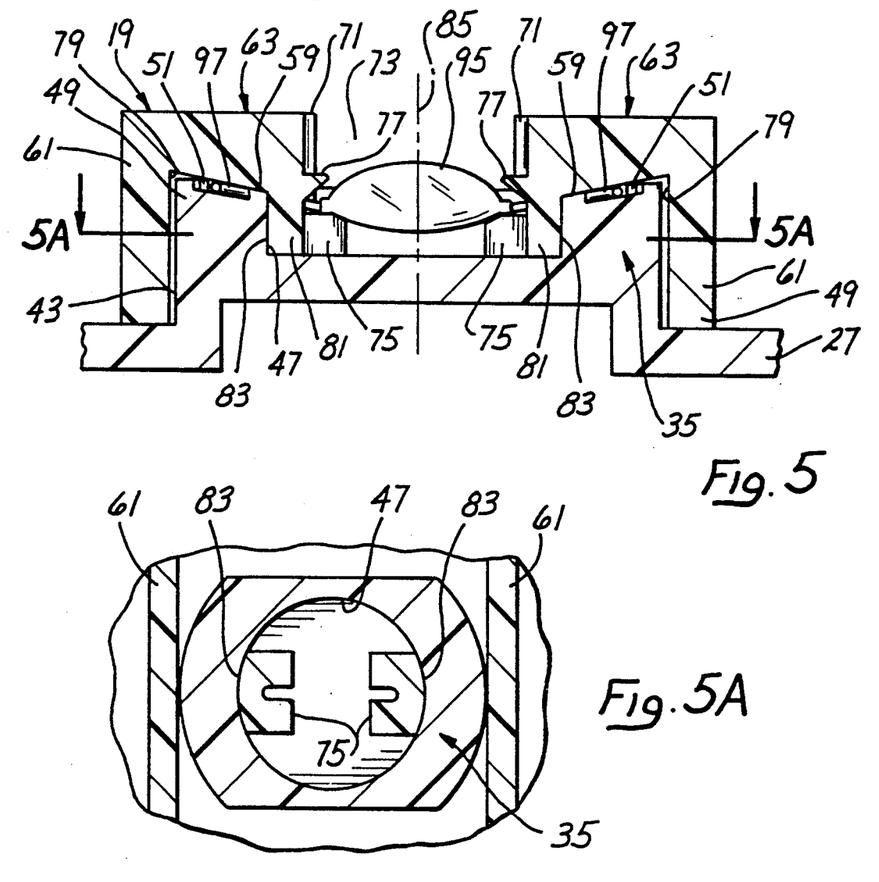
FIG. 5 is a sectional view taken generally along line 5 of FIG. 4.
FIG. 5A is a fragmentary sectional view taken along line 5A—5A of FIG. 5.

The retainer 35 has opposed part cylindrical walls 43 and opposed planar walls 45. The retainer 35 has a central cylindrical cavity 47 (FIGS. 2 and 5) such that the retainer has diametrically opposed curve projections 49 (FIG. 5). The projections 49 terminate in identical fixation member receiving sections 51 (FIGS. 2, 4 and 5). In this embodiment, each of the fixation member receiving sections 51 includes a groove 53, a shoulder 55, a curved support surface 57 and an abutment 59 extending upwardly (as viewed in FIGS. 2-5).

The folder 19 may be similar to the folder shown in Dulebohn U.S. Pat. No. 5,100,410. In this embodiment, the folder 19 includes elongated rails 61, jaws 63 integral with the rails 61, respectively, and projecting toward each other, and resiliently deformable, curved end sections 65 integrally and resiliently connecting the ends of the rails 61. With this construction, squeezing of the rails 61 moves the rails and the jaws 63 toward each other against the resilient biasing force of the end sections 65. Ridges 67 and 69 are provided on the opposite ends of the folder 19.

The jaws 63 have confronting surfaces 71 (FIG. 5) which define a well 73. Each of the jaws 63 has a ledge 75 at the bottom of the well 73 and a tab 77 above the associated ledge. The ledge 75 and the tab 77 are spaced apart axially, and they project into the well.

As shown in FIG. 5, the folder 19 has recesses 79 for receiving the projections 49 of the retainer. Each of the recesses 79 is defined by one of the rails 61, the associated jaw 63 and a depending flange portion 81 (FIG. 5) of the jaws. The jaws 63 partially close the upper ends of the grooves 53. The flange portions 81 have part circular outer bearing surfaces 83 (FIGS. 5 and 5A) which mate with the cylindrical surface of the cavity 47, and these surfaces cooperate to mount the folder 19 for pivotal movement on the retainer 35 about a pivot axis 85 (FIG. 5).

The cap 21 includes a cap portion 87 adapted to overlie the retainer 35 and a portion of the folder 19 as shown in FIG. 1. The cap 21 also includes opposed attachment legs 89 each having an outwardly turned flange 91 (FIG. 2) and opposed stabilizing legs 93. The attachment legs 89 and the flanges 91 thereof are sized to fit through the wide portions 41 (FIG. 3) of the slots 37 whereupon the cap 21 can be rotated clockwise as viewed in FIG. 3 to place the attachment legs 89 in the narrow portions 39 and the flanges 91 beneath the adjacent regions of the recessed portion 27. In this position, the stabilizing legs 93 engage the recessed portion 27 to firmly attach the cap 21 to the base 17. The cap 17 can be removed from the base by counterrotating the cap to bring the flanges 91 into registry with the wide portions 41 of the slots 37 whereupon the cap can be lifted off of the retainer 35 and the folder 19. When attached, the cap 27 firmly holds the folder 19 on the retainer 35 and completely covers and protects the IOL 15.

The lens case 13 can be used in association with a variety of IOL's 15. In the illustrated embodiment, the IOL 15 includes a deformable or foldable optic 95 (FIGS. 4 and 5) and two flexible, resilient, strand-like fixation members 97 affixed to the optic 95 at diametrically opposed locations.

As shown in FIGS. 3-5, the folder 19 receives the IOL 15, and more specifically the jaws 63 receive and support the deformable optic 95 at locations radially inwardly of the fixation member receiving sections 51. The jaws 63 loosely receive and support the IOL, and in particular the optic 95, for pivotal movement about the pivot axis 85 (FIG. 5) relative to the folder 19. Specifically, the deformable optic 95 rests on the ledges 75 and is held against upward movement off of the ledges by the tabs 77 which are spaced upwardly from the optic so the optic is loosely received to allow the relative pivotal movement between the IOL 15 and the folder 19 about the pivot axis 85.

In this position, the fixation members 97 are received by the fixation member receiving sections 51, respectively. Specifically, the fixation members 97 extend into the associated grooves 53 (FIGS. 4 and 5) and resiliently bear against the associated support surfaces 57.

The retainer 35 and in particular the fixation member receiving sections 51 hold the IOL 15 against substantial pivotal movement relative to the retainer about the pivot axis 85. More specifically, the projections 59 prevent pivotal movement of the IOL 15 in one direction about the pivot axis 85 and the shoulders 55 prevent substantial pivotal movement in the opposite direction about the pivot axis 85. As shown in FIG. 3, the fixation members 97 need not bear tightly against the shoulders 55 and/or the projections 59 and so some small pivotal movement of the IOL 15 may be permitted to occur. However, this is within the allowable tolerances for establishing the desired fold axes as discussed below.

For packaging purposes at the manufacturer's plant, the IOL 15 is loaded into the folder 19, and the folder 19 is then placed on the retainer 35 in the position of FIG. 3. The cap is then mounted on the base 17. In the position of FIG. 3, the ridges 67 and 69 are received in the grooves 33 and 29, respectively, to releasably retain the folder 19 in the 3 o'clock to 9 o'clock position.

In the position of FIGS. 3 and 4, the folder can be operated as described below to fold the deformable optic 95 about a fold axis 99 (FIG. 4) which extends generally from 3 o'clock to 9 o'clock. Using the same clock reference, the fixation members 97 in this embodiment are attached to the optic 95 at approximately 1:30 o'clock and 7:30 o'clock.

If the surgeon desires to fold the optic 95 about the axis 99 as shown in FIG. 4 and assuming that the cap 21 has been previously removed, the folder 19 is then removed from the base 17. Jaws 101 (FIG. 6) of IOL forceps 103 are placed into the well 73 just above the tab 77. The rails 61 are squeezed together to move the jaws 63 toward each other. This in turn moves the jaws 101 of the forceps toward each other and it folds the optic 95 generally about the fold axis 99. With the optic 95 folded between the jaws 101 of the forceps 103, the forceps can be used to remove the IOL from the folder 19. Thereafter, the IOL can be inserted in this folded condition through an incision into the eye.

Figure 7:
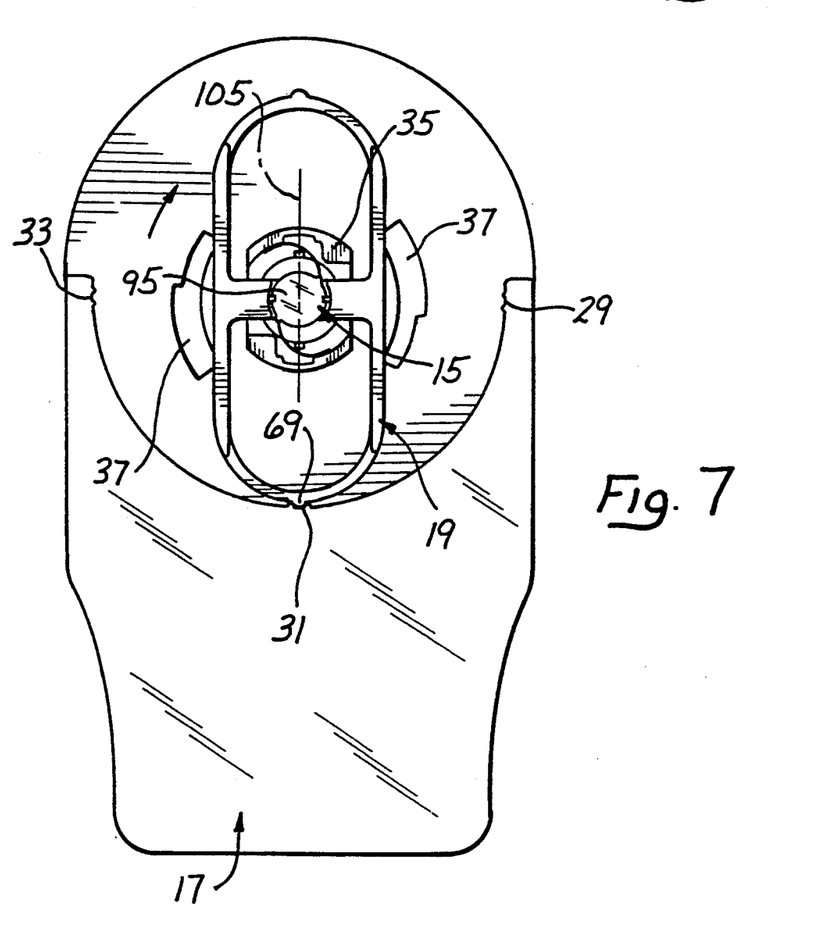
FIG. 7 is a plan view similar to FIG. 3 with the folder rotated to another position to change the orientation of the fold axis.
Figure 8:
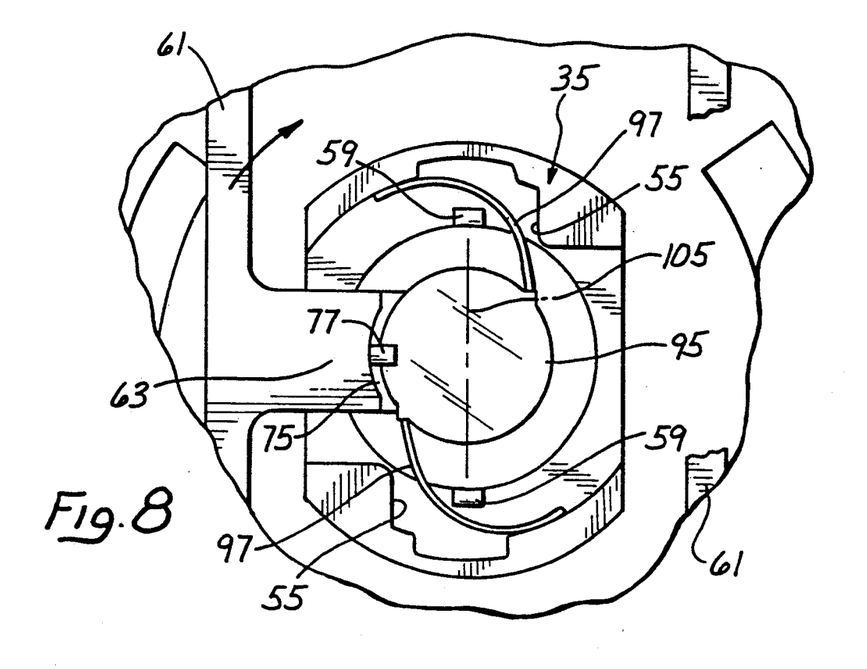
FIG. 8 is an enlarged view of the portion of FIG. 7 adjacent the IOL with portions of the folder broken away.

If the surgeon wishes to fold the optic 95 about a different fold axis 105 (FIGS. 7 and 8), the folder 19 is rotated about the pivot axis 85 to the position of FIGS. 7 and 8 in which the ridge 69 is received within the groove 31. The retainer 35 holds the IOL 15 against substantial pivotal movement relative to the retainer about the pivot axis 85. Specifically, if the folder 19 is pivoted 90 degrees in the clockwise direction to the position of FIG. 7, the shoulders 59 (FIG. 8) prevent the fixation members 97, and hence the IOL 15 from substantial pivotal movement about the pivot axis 85. To illustrate that the lens case 13 is adaptable to IOL's having fixation members of different configurations, the fixation members 97 are shown somewhat differently in FIGS. 4 and 8.

Figure 6:
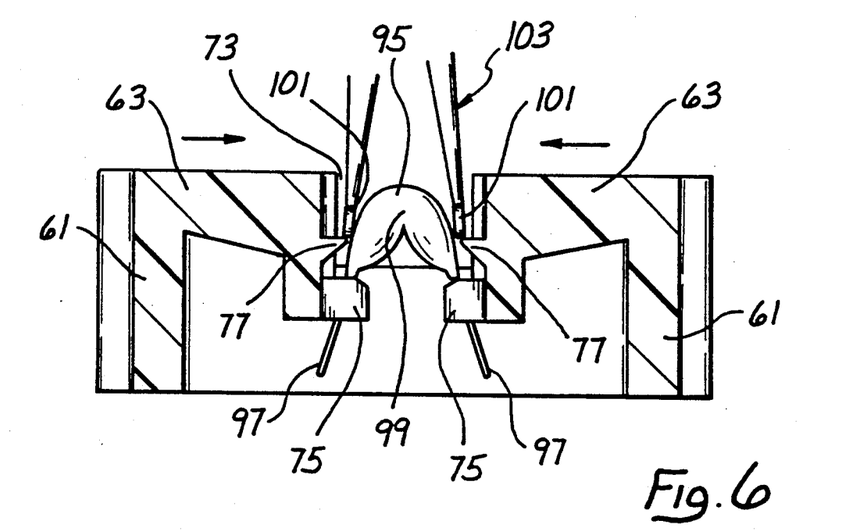
FIG. 6 is a sectional view similar to FIG. 5 with the folder removed from the base and being operated to fold the IOL.

In the position of FIGS. 7 and 8, the folder 19 can be removed from the retainer 35 and operated in the same manner as described below in connection with FIG. 6 to fold the optic 95 about the fold axis 105. It will be noted that the fold axis 105 extends from about 6 o'clock to about 12 o'clock and is displaced 90 degrees with respect to the fold axis 99 (FIG. 4). Alternatively, the fold axes 99 and 105 may be considered as the same fold axis in different angular positions. Of course, other fold axes at different angular orientations may be provided if desired. The two fold axes 99 and 105 are two commonly preferred axes. The fold axes 99 and 105 are transverse to each other and to the pivot axis 85. In this embodiment, the axes 99 and 105 and the pivot axis 85 are perpendicular to each other.

The grooves 29, 31 and 33 and the ridges 67 and 69 form a detent system for releasably retaining the folder 19 in any of a plurality of different angular positions about the pivot axis 85. If more than two fold axis positions are desired, additional grooves may be added to the curved wall 25 as desired.

Although an exemplary embodiment of the invention has been shown and described, many changes, modifications, and substitutions may be made by one having ordinary skill in the art without necessarily departing from the spirit and scope of the invention.

What is claimed is:

1. A lens case for an intraocular lens having a deformable optic, said lens case comprising:
   a folder for receiving the intraocular lens and folding the deformable optic about a fold axis;
   a retainer adjacent the folder for holding the intraocular lens against substantial pivotal movement relative to the retainer about a pivot axis which is generally transverse to the fold axis;
   the folder including jaws for loosely receiving and supporting the intraocular lens so as to allow relative pivotal movement of the folder and the intraocular lens about said pivot axis, and said jaws are relatively movable to fold the deformable optic about the fold axis; and
   the folder and retainer being mounted for relatively pivotal movement about said pivot axis whereby the orientation of the fold axis relative to the retainer can be changed.

2. A lens case as defined in claim 1 wherein the retainer has a fixation member receiving section for receiving a fixation member of the intraocular lens and holding the fixation member to thereby hold the intraocular lens against substantial pivotal movement relative to the retainer about said pivot axis and the jaws are adapted to receive and support the deformable optic at a location radially inwardly of the fixation member receiving section.

3. A lens case as defined in claim 1 wherein the folder is mounted for pivotable movement on the retainer about said pivot axis.

4. A lens case as defined in claim 1 wherein the retainer has a projection terminating in a fixation member receiving section for receiving a fixation member of the intraocular lens and holding the fixation member to thereby hold the intraocular lens against substantial pivotal movement relative to the retainer about said pivot axis and the folder has a recess for receiving the projection.

5. A lens case as defined in claim 1 wherein the retainer has a cavity and the folder has a bearing surface receivable in said cavity to mount the folder and retainer for relative pivotal movement about said pivot axis.

6. A lens case for an intraocular lens having a deformable optic, said lens case comprising:
a folder for receiving the intraocular lens and including jaws which are relatively movable to fold the deformable optic about a fold axis;
a base, the folder being mounted on the base for pivotal movement relative to the base about a pivot axis which is generally transverse to the fold axis; and
the base including a retainer for holding the intraocular lens against substantial pivotal movement about said pivot axis relative to the retainer whereby the orientation of the fold axis relative to the folder can be changed by relatively pivoting the folder and base.

7. A lens case as define din claim 6 further comprising cooperating surfaces on the retainer and folder for mounting the folder on the base for pivotal movement about said pivot axis.

8. A lens case as defined in claim 7 wherein the base has a curved wall at least partly circumscribing the retainer, and the lens case includes a detent system on the curved wall and the folder for releasably retaining the folder in any of first and second predetermined angular positions about the pivot axis.

9. A lens case as defined in claim 6 including a cap removably mounted on the base and having a cap portion overlying the retainer and at least a portion of the folder.

10. A lens case as defined in claim 6 wherein the folder is removably mounted on the base.

11. An IOL package comprising:
an intraocular lens having a deformable optic with an optical axis;
a folder for receiving the intraocular lens and folding the deformable optic about a fold axis which is generally transverse to the optical axis;
a retainer, said folder being on the retainer and being removable from the retainer, the retainer and the folder being mounted for relative pivotal movement generally about the optical axis while the folder is on the retainer;
the retainer holding the intraocular lens against substantial pivotal movement relative to the retainer generally about the optical axis so that the orientation of the fold axis relative to the retainer can be changed; and
said folder being capable of supporting and folding the deformable optic about the fold axis when the folder is removed from the retainer.

12. A package as defined in claim 11 wherein the intraocular lens includes at least one fixation member extending from the deformable optic and the retainer includes a fixation member receiving section for receiving said at least one fixation and holding the fixation member to thereby hold the intraocular lens against substantial pivotal movement relative to the retainer about said optical axis.

13. A method of folding an intraocular lens having a foldable optic with an optical axis along any of a plurality of fold axes, said method comprising:
supporting the intraocular lens on an IOL folder in a first angular position about a pivot axis so that the IOL folder can fold the foldable optic about a first fold axis;
retaining the intraocular lens against substantial pivotal movement about the pivot axis;
pivoting the IOL folder relative to the intraocular lens about the pivot axis to a second angular position so that the IOL folder can fold the foldable optic about a second fold axis;
folding the foldable optic about the second fold axis using the IOL folder; and
removing the intraocular lens from the IOL folder with the foldable optic folded about the second fold axis.

14. A method as defined in claim 13 including placing jaws of a forceps into the IOL folder adjacent the foldable optic, and the step of folding includes moving portions of the IOL folder toward each other to move the jaws of the forceps toward each other and to fold the foldable optic about the second fold axis, and the step of removing includes removing the foldable optic in a folded condition from the IOL folder using the forceps.

15. A method as defined in claim 13 wherein the step of retaining is carried out with a retainer, the folder and retainer are juxtaposed to allow relative pivotal movement about said pivot axis, and said method includes separating the folder and retainer after said step of pivoting and before said step of folding.

16. A lens case for an intraocular lens having a deformable optic, said lens case comprising:
a folder for receiving the intraocular lens and folding the deformable optic about a fold axis;
a retainer adjacent the folder for holding the intraocular lens against substantial pivotal movement relative to the retainer about a pivot axis which is generally transverse to the fold axis;
the folder and retainer being mounted for relative pivotal movement about said pivot axis whereby the orientation of the fold axis relative to the retainer can be changed; and
the retainer having a fixation member receiving section for receiving a fixation member of the intraocular lens and holding the fixation member to thereby hold the intraocular lens against substantial pivotal movement relative to the retainer about said pivot axis and the folder having jaws for receiving and supporting the deformable optic at a location radially inwardly of the fixation member receiving section.

17. A lens case for an intraocular lens having a deformable optic, said lens case comprising:
a folder for receiving the intraocular lens and folding the deformable optic about a fold axis;
a retainer adjacent the folder for holding the intraocular lens against substantial pivotal movement relative to the retainer about a pivot axis which is generally transverse to the fold axis;

the folder and retainer being mounted for relative pivotal movement about said pivot axis whereby the orientation of the fold axis relative to the retainer can be changed; and the retainer having a projection terminating in a fixation member receiving section for receiving a fixation member of the intraocular lens and holding the fixation member to thereby hold the intraocular lens against substantial pivotal movement relative to the retainer about said pivotal axis and the folder having a recess for receiving the projection.

18. A lens case for an intraocular lens having a deformable optic, said lens case comprising:

a folder for receiving the intraocular lens and folding the deformable optic about a fold axis;

a base, the folder being mounted on the base for pivotal movement relative to the base about a pivot axis which is generally transverse to the fold axis;

the base including a retainer for holding the intraocular lens against substantial pivotal movement about said pivot axis relative to the retainer whereby the orientation of the fold axis relative to the folder can be changed by relatively pivoting the folder and base;

the base having a curved wall at least partly circumscribing the retainer; and a detent system on the curved wall and the folder for releasably retaining the folder in any of first and second predetermined angular positions about the pivot axis.

19. A lens case for an intraocular lens having a deformable optic, said lens case comprising:

a folder for receiving the intraocular lens and folding the deformable optic about a fold axis;

a base, the folder being mounted on the base for pivotal movement relative to the base about a pivot axis which is generally transverse to the fold axis;

the base including a retainer for holding the intraocular lens against substantial pivotal movement about said pivot axis relative to the retainer whereby the orientation of the fold axis relative to the folder can be changed by relatively pivoting the folder and base; and a cap removably mounted on the base and having a cap portion overlying the retainer and at least a portion of the folder.

* * * * *

UNITED STATES PATENT AND TRADEMARK OFFICE
CERTIFICATE OF CORRECTION

PATENT NO. : 5,281,227
DATED : January 25, 1994
INVENTOR(S) : Glenn Sussman

It is certified that error appears in the above-identified patent and that said Letters Patent is hereby corrected as shown below:

```
Column 6, line 58 change "relatively" to -- relative --.

Column 7, line 34 change "define din" to -- defined in --.

Column 9, line 12 change "pivotal axis" to -- pivot axis --.
```

Signed and Sealed this

Thirtieth Day of August, 1994

Attest:

BRUCE LEHMAN

*Attesting Officer*    *Commissioner of Patents and Trademarks*